US011007328B2

(12) United States Patent
Chanie et al.

(10) Patent No.: US 11,007,328 B2
(45) Date of Patent: May 18, 2021

(54) MEDICINE INJECTION DEVICE WITH A PAIN-REDUCTION MEMBER

(71) Applicant: Ares Trading SA, Aubonne (CH)

(72) Inventors: Eric Chanie, Geneva (CH); Mahmut Tuncer, Melbourn (GB)

(73) Assignee: ARES TRADING SA, Aubonne (CH)

(*) Notice: Subject to any disclaimer, the term of this patent is extended or adjusted under 35 U.S.C. 154(b) by 355 days.

(21) Appl. No.: 15/035,994

(22) PCT Filed: Nov. 14, 2014

(86) PCT No.: PCT/EP2014/074557
§ 371 (c)(1),
(2) Date: May 11, 2016

(87) PCT Pub. No.: WO2015/071390
PCT Pub. Date: May 21, 2015

(65) Prior Publication Data
US 2016/0271341 A1 Sep. 22, 2016

(30) Foreign Application Priority Data

Nov. 14, 2013 (EP) .................................. 13005352
Apr. 24, 2014 (EP) .................................. 14165814

(51) Int. Cl.
*A61M 5/42* (2006.01)
(52) U.S. Cl.
CPC .............. *A61M 5/422* (2013.01); *A61M 5/42* (2013.01)
(58) Field of Classification Search
CPC ........ A61M 5/42; A61M 5/422; A61M 5/425; A61M 5/427; A61M 2205/59; A61H 2201/1695; A61H 2201/169
See application file for complete search history.

(56) References Cited

U.S. PATENT DOCUMENTS 4,373,526 A  2/1983 Kling
5,609,577 A * 3/1997 Haber ................ A61M 5/3243
604/110

(Continued)

FOREIGN PATENT DOCUMENTS

DE         8403816 U1   1/1986
DE    102004025651 A1  12/2005

(Continued)

OTHER PUBLICATIONS

PCT/EP2014/074557, International Search Report, dated Dec. 24, 2014, 14 pages.

*Primary Examiner* — Laura A Bouchelle
*Assistant Examiner* — Anh Bui
(74) *Attorney, Agent, or Firm* — Carter, DeLuca & Farrell LLP

(57) ABSTRACT

The injection device comprises a medicine container, means for injecting medicine from the medicine container to a patient through a needle, a skin contact surface crossable by the needle and having protrusions which are pressed around the injection site when the injection device is applied on the patient's skin for the injection, the protrusions being arranged so as to reduce the pain caused by the penetration of the needle, and a sensor for detecting contact of the patient's skin with the skin contact surface, wherein a predetermined force of application of the injection device on the patient's skin is required for the sensor to detect the patient's skin. According to another aspect of the invention, the protrusions include first and second protrusions, wherein the first protrusions come into contact with the patient's skin as the device is applied with a first force and the second protrusions come into contact with the patient's skin as the device is applied with a second force, the second force being greater than the first force.

9 Claims, 4 Drawing Sheets

(56) References Cited

U.S. PATENT DOCUMENTS

| | | |
|---|---|---|
| 6,171,276 B1 | 1/2001 | Lippe et al. |
| 7,284,293 B1 | 10/2007 | Holder et al. |
| 7,740,600 B2 | 6/2010 | Slatkine et al. |
| 2002/0013602 A1 | 1/2002 | Huttner |
| 2005/0033206 A1 | 2/2005 | Yeh |
| 2005/0054981 A1 | 3/2005 | Romano |
| 2006/0287664 A1* | 12/2006 | Grage, Jr. ........ A61B 5/150022 606/181 |
| 2012/0245497 A1* | 9/2012 | Nicholls ................ A61H 7/005 601/136 |
| 2013/0138013 A1 | 5/2013 | Hein et al. |
| 2013/0281882 A1 | 10/2013 | Cha |
| 2014/0074062 A1 | 3/2014 | Caffey |
| 2014/0142507 A1 | 5/2014 | Armes |

FOREIGN PATENT DOCUMENTS

| | | |
|---|---|---|
| DE | 102011015073 A1 | 9/2012 |
| EP | 2653101 A1 | 10/2013 |
| WO | 2005023088 A2 | 3/2005 |
| WO | 2007088444 A1 | 8/2007 |
| WO | 2014025796 A2 | 2/2014 |

* cited by examiner

MEDICINE INJECTION DEVICE WITH A PAIN-REDUCTION MEMBER

CROSS-REFERENCE TO RELATED APPLICATIONS

This application is a national stage filing of International Application No. PCT/EP2014/074557, filed Nov. 14, 2014, which claims benefit of priority pursuant to EP patent application no. 13005352.3, filed on Nov. 14, 2013 and EP patent application no. 14165814.6, filed Apr. 24, 2014. The entire disclosures of the afore-mentioned patent applications are incorporated herein by reference.

FIELD OF THE INVENTION

The present invention relates to an injection device for injecting medicine, typically in liquid form, to a patient. The present invention also relates to a pain-reduction member which equips or may equip such an injection device.

BACKGROUND OF THE INVENTION

It is known in the art to use a pain-reduction member in combination with an injection device to reduce the pain caused by the penetration of the injection device needle into the skin. U.S. Pat. No. 6,902,554 and US 2005/0054981 disclose pain-reduction members in the form of a plate bearing protrusions on one of its surfaces. The plate has a through hole for passage of a syringe needle. When pressed against the skin, the protrusions stimulate large-diameter sensory nerve fibres proximate the injection site and block the pain signals from the small-diameter pain nerve fibres. The protrusions also draw the patient's attention away from the needle penetration into the skin.

A first problem with such known devices is that nothing obliges the patient to sufficiently press the pain-reduction member on the skin. If the said member is not sufficiently pressed, the pain reduction effect will be negligible.

A second problem is that the patient cannot adjust the type of sensation provided by the protrusions.

To remedy the first problem, the present invention provides according to a first aspect an injection device comprising:
- a medicine container,
- means for injecting medicine from the medicine container to a patient through a needle,
- a skin contact surface crossable by the needle, said skin contact surface having protrusions which are pressed around the injection site when the injection device is applied on the patient's skin for the injection, said protrusions being arranged so as to reduce the pain caused by the penetration of the needle, and
- a sensor for detecting contact of the patient's skin with the skin contact surface, wherein a predetermined force of application of the injection device on the patient's skin is required for the sensor to detect the patient's skin.

Typically, the predetermined force of application of the injection device on the patient's skin is higher than the weight of the injection device.

The sensor is e.g. a capacitive or mechanical sensor.

In an embodiment, said protrusions comprise a set of first protrusions and a set of second protrusions.

Typically, the second protrusions have a smaller dimension, in the direction of the needle, than the first protrusions.

Advantageously, the second protrusions have sharper tips than the first protrusions.

To remedy the second problem mentioned above, i.e. to enable the patient to change the sensation provided by the protrusions, the present invention provides according to a second aspect an injection device comprising:
- a medicine container,
- means for injecting medicine from the medicine container to a patient through a needle, and
- a skin contact surface crossable by the needle, said skin contact surface having protrusions which are pressed around the injection site when the injection device is applied on the patient's skin for the injection, said protrusions being arranged so as to reduce the pain caused by the penetration of the needle, wherein said protrusions comprise a set of first protrusions and a set of second protrusions, wherein:
  (i) the first protrusions come into contact with the patient's skin as the device is applied with a first force and the second protrusions come into contact with the patient's skin as the device is applied with the second force, the second force being greater than the first force; and/or
  (ii) the first and second protrusions are configured such that the second protrusions engage the skin of the user subsequent to the engagement of the first protrusions when the device is subject to a pressing force above a predetermined amount.

Typically, the second protrusions have a smaller dimension, in the direction of the needle, than the first protrusions.

Advantageously, the second protrusions have sharper tips than the first protrusions.

Preferably, the first and second protrusions are arranged on the skin contact surface in a mixed manner, more precisely in a separated and interspersed manner.

In a particular embodiment, the first protrusions are arranged on first circles, the second protrusions are arranged on second circles, concentric with the first circles, and the first and second circles are arranged in an alternating manner.

In both aspects of the invention:
  the protrusions may extend in the direction of the needle,
  the protrusions may be in the form of spikes,
  the injection device may comprise a member removably mounted on a housing of the injection device and defining the skin contact surface and its protrusions,
  the skin contact surface may further comprise feet which are arranged to rest on a flat surface, together with at least some of the protrusions (typically the first protrusions), when the injection device is placed on said flat surface,
  the feet may have the same dimension, in the direction of the needle, than at least some of the protrusions (typically the first protrusions).

The above-mentioned member may be elastically mounted on said housing and, to this effect, may comprise elastic tabs.

The above-mentioned member may comprise another through hole in a region facing the sensor.

The above-mentioned member may be transparent and/or in the form of a plate.

The above-mentioned member may be larger in width and length than a bottom wall of the injection device.

The present invention further provides a device to apply a pressing force to a skin of a user proximate to an injection zone comprising a plurality of first protrusions arranged to engage the skin of the user, characterised in that the device further comprises a plurality of second protrusions, wherein:
 (i) the first and second protrusions are configured such that the second protrusions engage the skin of the user subsequent to the engagement of the first protrusions when the device is subject to a pressing force above a predetermined amount; and/or
 (ii) the first protrusions come into contact with the patient's skin as the device is applied with a first force and the second protrusions come into contact with the patient's skin as the device is applied with the second force, the second force being greater than the first force.

Typically, the second protrusions have a smaller dimension, in the direction of the pressing force, than the first protrusions.

Advantageously, the second protrusions have sharper tips than the first protrusions.

It is noted that the protrusions of the invention do not pierce the skin. The protrusions depress the skin.

In any of the injection devices or the device to apply a pressing force as defined above, the protrusions may have a height within 1.8 mm and 3.3 mm, a base diameter within 0.9 mm and 1.8 mm and a tip radius within 0.2 mm and 0.7 mm. The first protrusions may have a height of about 3 mm, a base diameter of about 1.6 mm and a tip radius of about 0.5 mm and the second protrusions may have a height of about 2 mm, a base diameter of about 1 mm and a tip radius of about 0.3 mm.

The present invention further provides a method for injecting medicine to a patient using any of the devices defined above, the method comprising the steps of pressing the protrusions against the patient's skin and performing the injection.

BRIEF DESCRIPTION OF THE DRAWINGS

Other features and advantages of the present invention will become apparent upon reading the following detailed description made with reference to the appended drawings in which.

DETAILED DESCRIPTION

Figure 1:
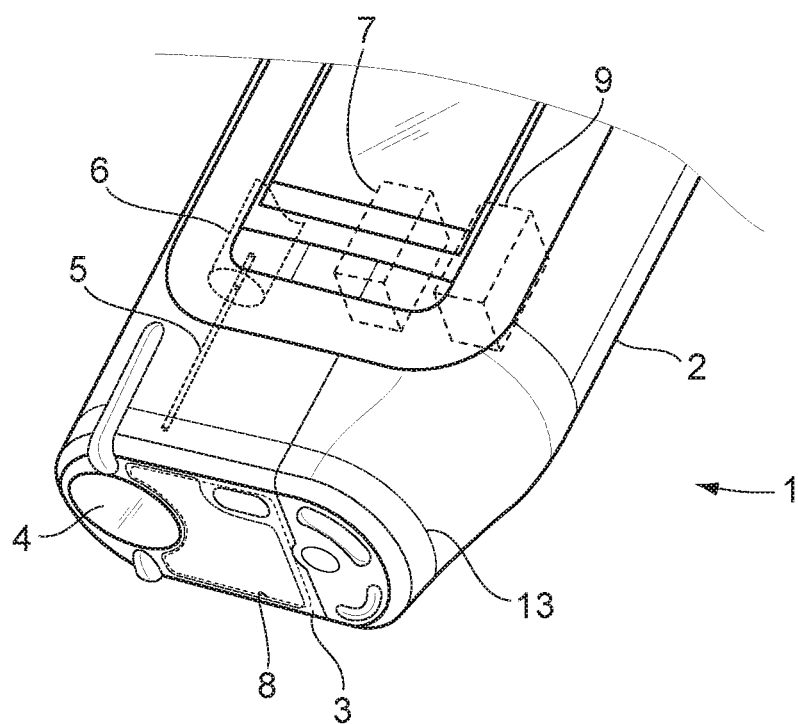
FIG. 1 is a partial perspective view of an injection device.

FIG. 1 shows a medicine injection device 1 of the type disclosed in WO 2005/077441 and WO 2007/088444. This injection device 1 comprises a housing 2 having a bottom wall 3. A through hole 4 in the bottom wall 3 permits passage of a needle 5. The needle 5 is connected to a medicine container 6 inside the housing 2. A mechanism 7, including an electric motor, is also provided inside the housing 2 for holding and moving vertically the medicine container 6 with its needle 5 so that these elements 5, 6 can take a retracted position, fully inside the housing 2, and an operating position in which the needle 5 protrudes from the through hole 4 to pierce the skin of a patient. The mechanism 7 further controls movement of a piston in the medicine container 6 to perform the injection after the needle 5 has pierced the patient's skin. A skin sensor 8 is provided in or near the bottom wall 3 to detect proximity of human skin to the said wall. The skin sensor 8 may be capacitive, as disclosed in WO 2007/088444, or of a different type, such as mechanical. An electronic control unit 9 in the housing 2 allows piercing of the patient's skin by the needle 5 and injection of medicine only after the skin sensor 8 has detected that the injection device 1 is placed on the skin.

Figure 2:
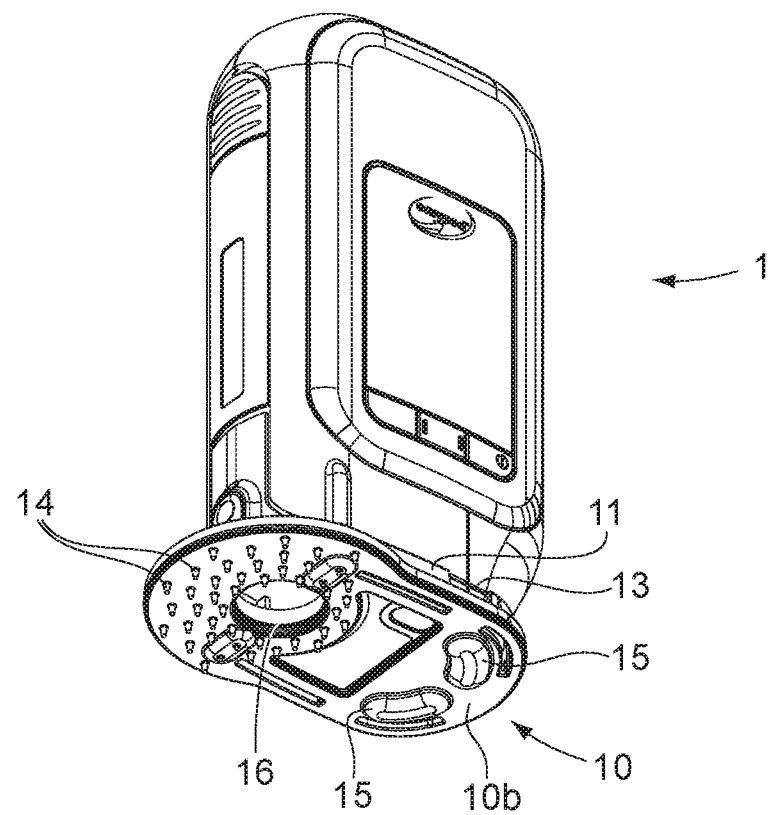
FIG. 2 is a perspective view of the injection device fitted with a pain-reduction member.
Figure 3:
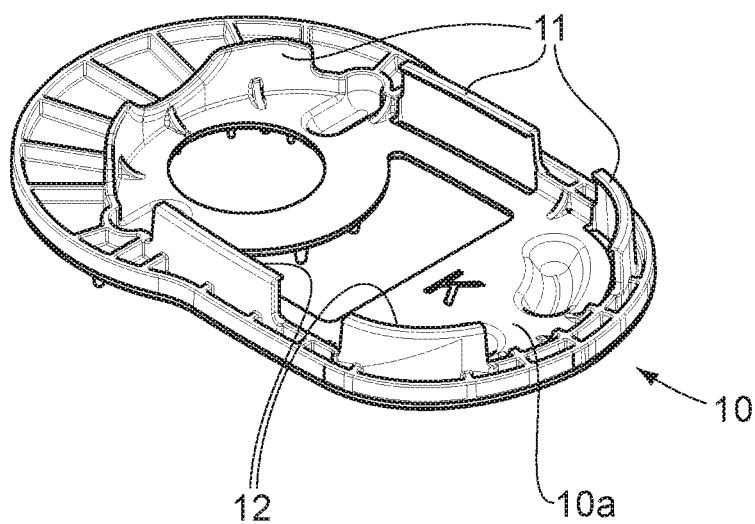
FIG. 3 is a top perspective view of the pain-reduction member.
Figure 4:
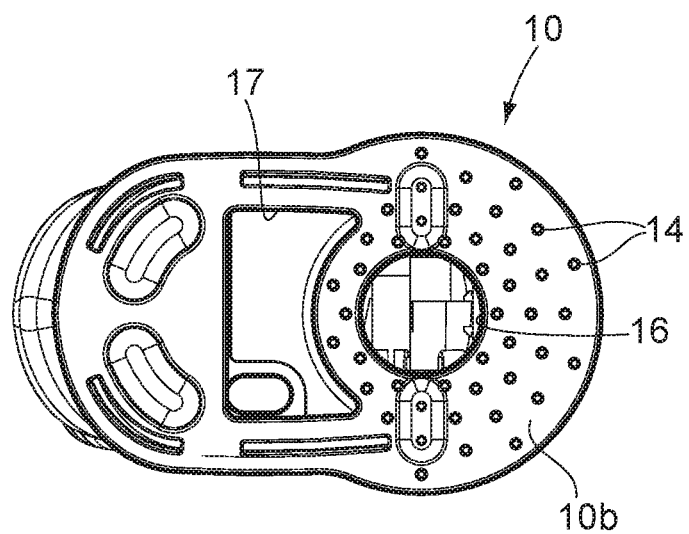
FIG. 4 is a bottom plane view of the injection device fitted with the pain-reduction member.

In order to reduce the pain caused by the penetration of the needle 5 into the patient's skin, the injection device 1 may be fitted with a pain-reduction member 10 as shown in FIGS. 2 and 3. The pain-reduction member 10 is in the form of a plate mountable against the bottom wall 3. On a peripheral portion of one, 10a, of its two surfaces, the pain-reduction member 10 has tabs 11 which form a sleeve receiving the bottom portion of the injection device 1. At least some of the tabs 11 are elastically deformable and have curved ends 12 which may engage a groove 13 of the housing 2 to hold the pain-reduction member 10 against the bottom wall 3. The pain-reduction member 10 may thus be easily attached to/detached from the injection device 1. On its surface 10b opposite the one 10a bearing the tabs 11, the pain-reduction member 10 has protrusions including spikes 14 and feet 15 (see FIGS. 2 and 4). The surface 10b with its spikes 14 and feet 15 forms the skin contact surface of the injection device 1, intended to contact the patient's skin around the injection site, when the injection device 1 is fitted with the pain-reduction member 10.

The skin contact surface 10b is preferably substantially flat, as represented, but could also be curved. The pain-reduction member 10 further has first and second through holes 16, 17. The first through hole 16 is aligned with the through hole 4 of the bottom wall 3 and its function is thus to let the needle 5 pass for the injection. The second through hole 17 faces the skin sensor 8 and avoids the pain-reduction member 10 disturbing the skin detection. One or both of the through holes 4, 16 which allow passage of the needle 5 may be closed by a pierceable membrane.

The spikes 14 are arranged around the passage of the needle 5, i.e., in bottom view (see FIG. 4), around the through hole 16, and extend in the direction of the needle 5. More precisely, the spikes 14 are arranged on several concentric circles that are coaxial with the through holes 4, 16. Thus, when the injection device 1 is placed on the skin for the injection, the spikes 14 are pressed against the skin around the injection site to provide the pain-reduction effect upon the needle 5 penetrating the skin. The density and spacing of the spikes 14 are selected to stimulate the large-diameter sensory nerve fibres proximate the injection site and to block the pain signals from the small-diameter pain nerve fibres. Blocking the pain signals include totally or partially blocking, saturating or desensitising the nerve signals. The spikes 14 also draw the patient's attention away from the needle penetration into the skin. To increase the pain-reduction effect, the pain-reduction member 10 has larger width and length than the bottom wall 3, as is visible in FIG. 2. In order for the patient to keep a good visibility of the through hole 4 from which the needle 5 will protrude for the injection, the pain-reduction member 10 is made of a transparent material.

The feet 15 are located in a region of the pain-reduction member 10 that is furthest from the through hole 16 and have the same height as the spikes 14. In combination with the spikes 14, the feet 15 allow the pain-reduction member 10 to be stable and horizontal when placed on a horizontal surface.

The material of the pain-reduction member 10 is preferably a polymer such as polypropylene (preferably of the homopolymer type) and is typically made as a one-piece device, e.g. by a moulding process.

According to an advantageous feature of the invention, when the injection device 1 is fitted with the pain-reduction member 10, a predetermined force of application of the injection device 1, 10 on the skin is required for the skin sensor 8 to detect the skin and therefore to allow the injection. In other words, to perform the injection the patient must apply the injection device 1, 10 on the skin with sufficient force. The predetermined force of application of the injection device 1, 10 on the skin is typically higher than the weight of the injection device 1, 10, i.e. than the force of gravity applied on the injection device 1, 10. This ensures that the spikes 14 will be sufficiently pressed against the skin to efficiently reduce the pain associated with the penetration of the needle 5 into the skin. If the skin sensor 8 is a capacitive sensor, its sensitivity is determined by features such as the shape and size of the measuring electrode(s) and the capacitive change detection threshold of the corresponding electronic circuit. Particularly, for given shape and size of the electrode(s), it is possible to adjust the threshold from which it is considered that a detected capacitive change indicates that the injection device 1 is properly placed on the skin. In the present invention, the sensitivity of the skin sensor 8 is thus set at a sufficiently low value to achieve the desired effect, i.e. to require a sufficient pressure to be exerted by the spikes 14 on the skin to reach the detection threshold. If the skin sensor 8 is mechanical, the said effect may be achieved by suitably positioning a movable contact of the sensor between the bottom wall 3 and the reference plane defined by the tips of the spikes 14 and feet 15.

Figure 5:
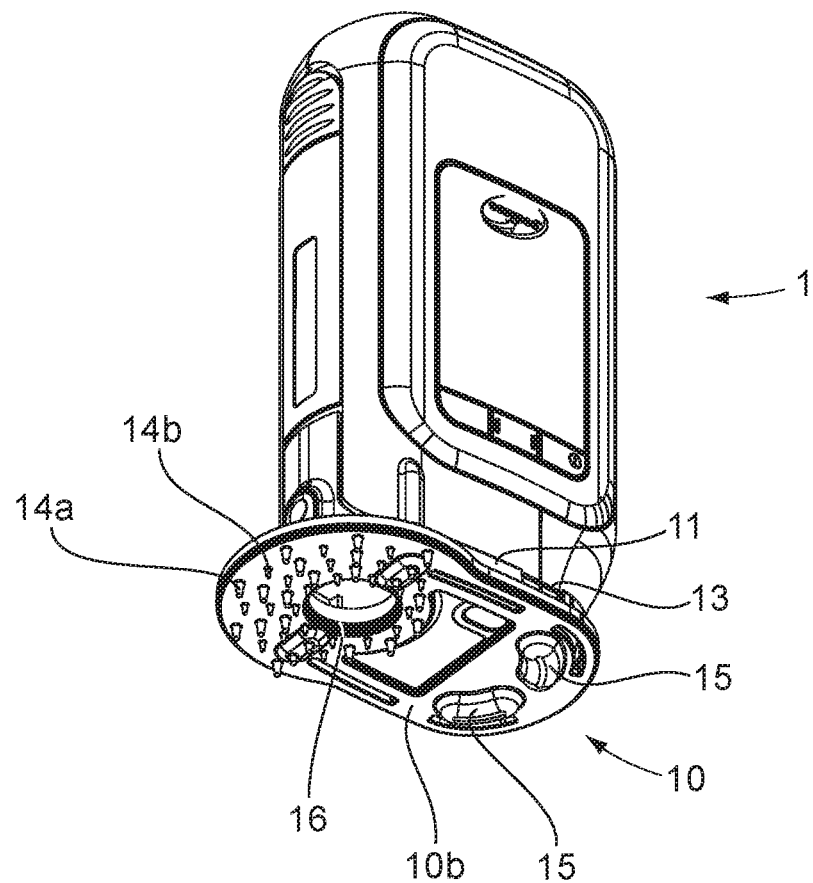
FIG. 5 is a perspective view of the injection device fitted with a pain-reduction member according to a variant of the invention.
Figure 6:
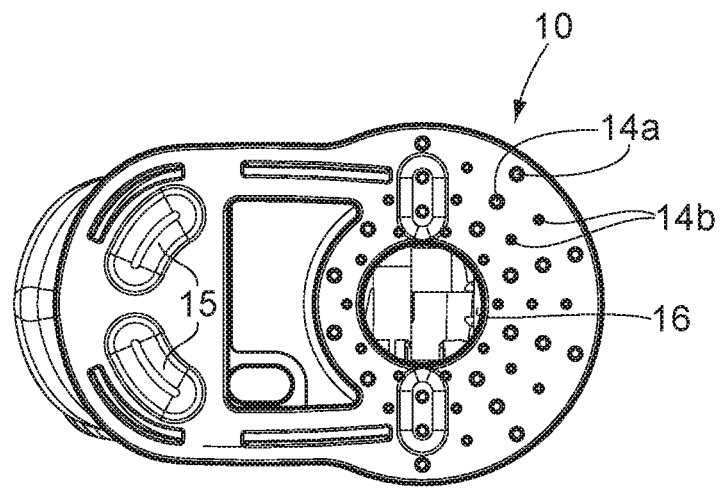
FIG. 6 is a bottom plane view of the injection device fitted with the pain-reduction member according to the said variant of the invention.

According to a variant of the invention, shown in FIGS. 5 and 6, the spikes 14 include first spikes 14a and second spikes 14b. The first spikes 14a have the same height as the feet 15. The second spikes 14b, on the other hand, have a smaller height (or length) than the first spikes 14a so that when the pain-reduction member 10 is placed on a flat rigid surface, the tips of the first spikes 14a rest on the surface (together with the feet 15) while the second spikes 14b do not contact the surface. Thus, when the pain-reduction member 10 is placed on the patient's skin, upon applying a first force on the member 10 the patient will essentially feel the first spikes 14a and upon applying a second force higher than the first force the patient will feel both the first and second spikes 14a, 14b. Moreover, preferably, the tips of the second spikes 14b are sharper than the tips of the first spikes 14a so as to provide a pricklier effect on the patient than the first spikes 14a. By applying the aforementioned second force the patient will have a different sensation than by applying only the first force. The patient may thus choose which one of the sensations he/she wants. Particularly, if the sensation provided by the first spikes 14a is judged not sufficient for reducing the pain caused by penetration of the needle 5 into the skin, the patient may decide to more strongly press the injection device 1 and pain-reduction member 10 on his/her skin so as to feel a greater number of spikes, including the sharper-tip second spikes 14b.

In an alternative embodiment, the skin contact surface 10b is curved such that a first portion of the skin contact surface is displaced from the injection device 1 and a second portion of the skin contact surface is adjacent to the injection device 1. On the skin contact surface 10b opposite the surface 10a bearing the tabs 11, the pain-reduction member 10 has protrusions including spikes 14. The displaced portion of the skin contact surface has a first set of spikes protruding therefrom. The adjacent portion of the skin contact surface has a second set of spikes protruding therefrom. In this embodiment the first and second sets of spikes have the same height as each other. However, the first set of spikes reach further away from the injection device given that they protrude from a surface that is displaced from the injection device.

In this alternative embodiment the first spikes have the same height as the feet 15 so that when the pain-reduction member 10 is placed on a flat rigid surface, the tips of the first spikes rest on the surface (together with the feet 15) while the second spikes do not contact the surface. Thus, when the pain-reduction member 10 is placed on the patient's skin, upon applying a first force on the member the patient will essentially feel the first spikes and upon applying a second force higher than the first force the patient will feel both the first and second spikes.

Figure 7:
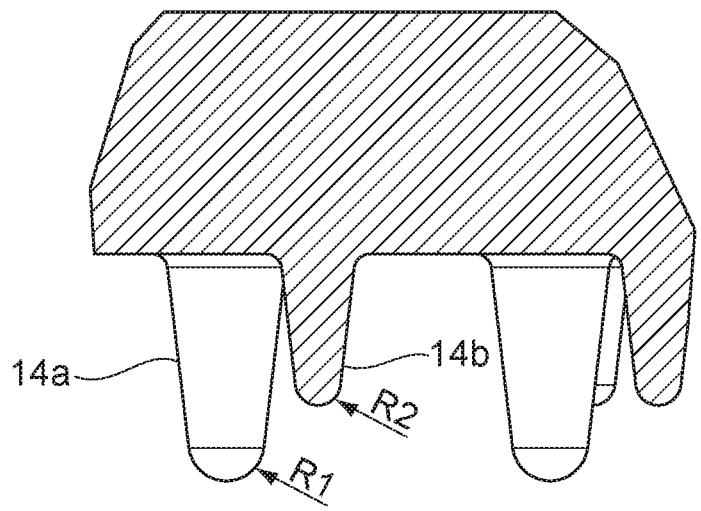
FIG. 7 is a partial sectional view of the pain-reduction member according to the said variant of the invention.
Figure 8:
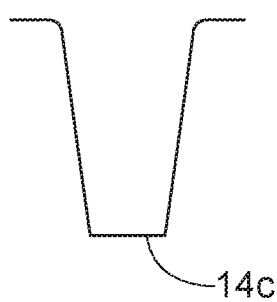
FIG. 8 is a diagrammatic view showing an alternative shape of a spike of the pain-reduction member.

The sharpness of the tips of the spikes 14a, 14b is defined by the area of the surface that comes into contact with the skin. The smaller the surface area of the tip, the sharper the tip. In the case of conical spikes with spherical tips as shown in FIG. 7, a sharper tip is a tip whose radius is smaller. Thus, in this case, the radius R2 of the tips of the second spikes 14b is preferably smaller than the radius R1 of the tips of the first spikes 14a. If desired, the radii R1, R2, or only the radius R2, may be very small such that the corresponding tips may approximate perfect, discrete points. However, many other shapes are possible for the spikes 14a, 14b, such as truncated spikes with flat tips 14c as shown in FIG. 8.

Preferably, the first and second spikes 14a, 14b are mixed to each other. The first and second spikes 14a, 14b may be on respective concentric circles that are coaxial with the trough holes 4, 16, with the concentric circles for the first spikes 14a alternating with the concentric circles for the second spikes 14b as visible in FIG. 6.

In further embodiments, more than two sets of spikes could be provided. In particular, a set of third spikes could be provided which would have a smaller height than the second spikes 14b so as to engage the patient's skin when the pain-reduction member 10 is applied with a third force greater than the second force required for the second spikes 14b to engage the skin. The third spikes could have sharper tips than the second spikes 14b.

In the invention as described above, the injection device 1 and the pain-reduction member 10 are two separate devices that can be assembled to one another. In a variant however, the pain-reduction member 10 could be integral with the housing 2 of the injection device 1.

The present invention as described above is particularly effective in reducing the pain caused by the penetration of the needle for patients having low pain tolerance. Tests have been carried out among ten subjects having the following characteristics:

| Category | | Value |
|---|---|---|
| Age (years) | Mean ± standard deviation | 30 ± 5 |
| | Range | 23-40 |
| Gender | Female | 10 (100%) |
| Race | Caucasian | 10 (100%) |
| Body mass index (kg/m$^2$) | Mean ± standard deviation | 24.4 ± 2.8 |
| | Range | 19.4-29.0 |

Among these ten subjects, six met the pre-specified definition of a low pain tolerance and were the focus of the analysis. These six subjects, immediately after receiving an injection of a placebo dose with the injection device 1 not fitted with the pain-reduction member 10, assessed pain scores higher than 30 mm on a 100 mm Visual Analogue Scale (VAS).

Successive injections of placebo doses were carried out on each of these six subjects, with an injection device respectively fitted with pain-reduction members A, B, C, the order of the pain-reduction members A, B, C being randomly changed from one subject to another. For each subject the elapsed time between two successive injections was 30 minutes and the injections were alternatively made on the right and the left arms on different injection sites. Immediately after an injection (within 5 minutes), the subject indicated the magnitude of the pain associated with the injection she just received, by drawing a line on the Visual Analogue Scale.

Figure 9:
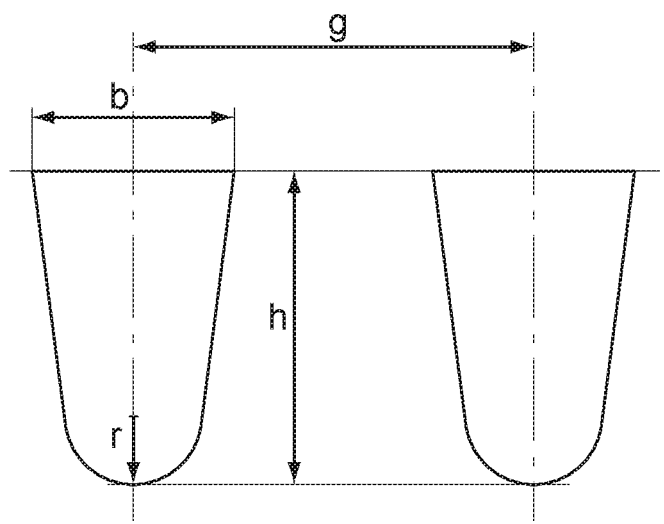
FIG. 9 is a diagrammatic view showing how spike dimensions of the pain-reduction member are measured.

The pain-reduction members A, B, C are distinguished from one another by the dimensions of their spikes. The pain-reduction members A and B are of the type shown in FIGS. 2 to 4, i.e. they each have only one size of spikes 14. The pain-reduction member C, on the other hand, is of the type as shown in FIGS. 5 to 7, i.e. it has two sizes of spikes 14a, 14b. With reference to FIG. 9, the dimensions of the spikes of the pain-reduction members A, B, C are detailed in the table below:

| Dimensions (in mm) | A | B | C |
|---|---|---|---|
| spacing (g) | ~5 (4.1-6.6) | ~5 (4.1-6.6) | ~5 (4.1-6.6) |
| height (h) | 2 | 3 | 3/2 |
| base diameter (b) | 1.2 | 1.6 | 1.6/1 |
| tip radius (r) | 0.4 | 0.6 | 0.5/0.3 |

For the six subjects the pain felt during an injection was lower when the injection device was fitted with one of the pain-reduction members A, B, C than when the injection device was not fitted with any pain-reduction member. The mean difference between the value on the Visual Analogue Scale when the injection device was fitted with one of the pain-reduction members A, B, C and the value on the Visual Analogue Scale when the injection device was not fitted with any pain-reduction member is indicated in the table below:

| Pain-reduction member | Mean absolute VAS change (mm) |
|---|---|
| A | −8 |
| B | −10 |
| C | −15 |

The same mean difference, but expressed as a percentage of the value on the Visual Analogue Scale noted after an injection performed without a pain-reduction member, is indicated in the table below:

| Pain-reduction member | Mean relative VAS change (%) |
|---|---|
| A | −11 |
| B | −14 |
| C | −22 |

It can be seen in particular that the pain-reduction member C, with its spikes of different heights, base diameters and tip radii, provides the best results. The VAS score is reduced by 15 mm and by 22% with respect to the VAS score obtained with the injection device not fitted with a pain-reduction member.

The invention claimed is:

1. An injection device comprising:
a medicine container;
means for injecting medicine from the medicine container to a patient through a needle; and
said injection device fitted with a pain reduction member comprising a skin contact surface crossable by the needle, said skin contact surface having protrusions which are pressed around the injection site when the injection device is applied on the patient's skin for the injection, said protrusions being arranged so as to reduce the pain caused by the penetration of the needle;
wherein said protrusions comprise a set of first protrusions and a set of second protrusions, wherein the first protrusions come into contact with the patient's skin as the device is applied with a first force and the second protrusions come into contact with the patient's skin as the device is applied with a second force, the second force being greater than the first force;
wherein the first protrusions are arranged on first circles, the second protrusions are arranged on second circles, concentric with the first circles, and the first and second circles are arranged in an alternating manner;
wherein the first and second protrusions are arranged in alternating columns radiating from the hole through which the needle passes for injection; and
wherein the protrusions are in the form of spikes, and wherein the second protrusions have sharper tips than the first protrusions.

2. The injection device according to claim 1, wherein the second protrusions have a smaller dimension, in the direction of the needle, than the first protrusions.

3. The injection device according to claim 1, wherein the first and second protrusions are arranged on the skin contact surface in a mixed manner.

4. The injection device according to claim 1, wherein the pain reduction member is a member removably mounted on a housing of the injection device and defining the skin contact surface and its protrusions.

5. The injection device according to claim 4, wherein the member is elastically mounted on said housing.

6. The injection device according to claim 4, wherein the member is transparent.

7. The injection device according to claim 4, wherein the member is in the form of a plate.

8. The injection device according to claim 1, wherein the skin contact surface further comprises feet which are arranged to rest on a flat surface, together with at least some of the protrusions, when the injection device is placed on said flat surface.

9. The injection device of claim 1, wherein the pain reduction member comprises tabs.

* * * * *